(12) United States Patent
Landreth (10) Patent No.: US 6,265,879 B1
(45) Date of Patent: Jul. 24, 2001

(54) ELECTRICAL INTEGRITY TEST SYSTEM FOR BOATS

(76) Inventor: Keith W. Landreth, 5701 Hadrian Dr., Durham, NC (US) 27703

( * ) Notice: Subject to any disclaimer, the term of this patent is extended or adjusted under 35 U.S.C. 154(b) by 0 days.

(21) Appl. No.: 09/353,324

(22) Filed: Jul. 14, 1999

(51) Int. Cl.$^7$ .......................... H01H 31/02; G01N 27/00
(52) U.S. Cl. ............................... 324/537; 324/71.2
(58) Field of Search ..................... 324/537, 763, 324/767, 71.1, 71.2

(56) References Cited

U.S. PATENT DOCUMENTS

| | | |
|---|---|---|
| 5,747,892 | 5/1998 | Staerzl . |
| 5,748,008 | 5/1998 | Landreth . |
| 5,751,530 | 5/1998 | Pelly et al. . |
| 5,856,904 * | 1/1999 | Pelly et al. .......................... 361/111 |

* cited by examiner

*Primary Examiner*—Safet Metjahic
*Assistant Examiner*—J. Kerveros
(74) *Attorney, Agent, or Firm*—Olive & Olive, P.A.

(57) ABSTRACT

An electrical integrity test system for boats provides circuitry for evaluating the integrity of the boat's galvanic isolator. The integrity test system includes two single reference diodes and a circuit for applying DC voltages across said reference diodes and said galvanic isolator. Another micro-controller stores the values of the voltage drops across the galvanic isolator and the voltage drops across each reference diode and subsequently determines if the voltage drop across the galvanic isolator is that to be normally expected. If it is not, then the system informs the operator that the boat's galvanic isolator is not operating properly.

26 Claims, 2 Drawing Sheets

ELECTRICAL INTEGRITY TEST SYSTEM FOR BOATS

BACKGROUND OF THE INVENTION

1. Field of the Invention

This invention relates to circuitry that evaluates and monitors electrical systems, in particular the integrity of a boat's galvanic isolator.

2. Background of the Prior Art

When boats or marine craft are docked and are connected to a dock's AC electric distribution system typically comprised of hot, neutral and grounding conductors, a number of potential dangers exist. Although a boat may be correctly wired, an inadequate or disconnected grounding conductor on the boat, or reversed polarity of the dock's AC electrical distribution system, poses a danger to electrical components on the boat. A more serious danger is that of electric shock to individuals in the boat, or possible death by drowning of individuals in the water. The electric shock hazard exits as a result of inadequate AC grounding systems causing normal stray AC leakage and possible fault currents to flow through exposed metal boat components and through the water or through individuals in contact with an adequate ground.

A boat typically includes AC powered appliances including battery chargers, refrigerators, air conditioners, and the like. A boat battery supplies DC power to DC powered devices such as engine starting motors, navigation equipment, running lights, and the like. A boat's AC safety ground and DC powered devices are bonded at a common point at the boat's DC ground, which is normally the boat's engine. For the purposes of this description, a boat's grounding system is referred to as the AC grounding system. As a boat's AC and DC electrical systems are bonded at a common point, it is understood that the AC grounding system includes a boat's negative DC electrical system.

Boats connected to a dock's electrical distribution system share that system's common earth ground. This common ground acts to electrically connect the boats together. When two or more of these boats are connected via a dock's electrical system, a galvanic cell can be established between different underwater metal parts of these boats. Galvanic action results and what is referred to as DC galvanic current flows through the water between adjacent boats and through the commonly shared AC grounding conductor. This galvanic action can corrode a boat's underwater metal parts, and possibly sink a boat. The degree of corrosion is dependent on a number of parameters, such as the salinity of the water, electric current density, surface area and nature of the underwater metals, etc.

A common device used to block galvanic current is the galvanic isolator. The galvanic isolator is serially installed in the boat's AC grounding conductor, usually immediately adjacent or within close proximity to the boat's power inlet. The galvanic isolator is typically comprised of two sets of opposing pairs of silicon diodes and an optional capacitor in parallel with the two diode sets, which are enclosed in a metal or plastic housing. The threshold voltage at which diodes are biased varies among diodes. Typically all silicon diodes start conducting current at a voltage level as low as 0.4 to 0.45 volts and are assumed to be in full conduction at approximately 0.6 volts to 0.8 volts. Therefore, the diode pairs of a galvanic isolator start conducting at 0.9 to 0.95 volts and are fully biased at 1.20 to 1.6 volts.

The primary purpose of the galvanic isolator is to block all DC galvanic currents in both directions, but provide a path for AC leakage or fault currents back to the dock's power system earth ground. The sets of diodes, and the capacitor, if one is provided, are electrically insulated from the boat. However, one side of the galvanic isolator is connected to the boat's negative engine terminal, or DC ground, which electrically bonds the negative side of the boat's DC system and the AC grounding system together, and its other side is connected by the boat's AC grounding conductor to the AC grounding pin on the boat's power inlet.

Galvanic isolators are relatively inexpensive, compact, and light. However, the integrity of galvanic isolators can be compromised in a number of ways. For example, a faulty open diode or open capacitor of a galvanic isolator would normally prevent or block DC galvanic currents from flowing, but may not pass AC leakage or fault currents back to the dock electrical system. These currents may nevertheless find an alternative path to ground, possibly through the boat's out-drive, through the water and adjacent boats to the dock's earth ground, thus endangering persons in the water and on other boats.

Even if a galvanic isolator is initially operable, limited fault currents may not immediately trip the dock's circuit breaker, but may create high temperatures within the galvanic isolator and pose a fire hazard. The high temperature may cause the galvanic isolator diode(s) to short (or open). A shorted diode compromises the ability of the galvanic isolator to effectively block DC galvanic currents.

Typically, the integrity of a galvanic isolator is not checked until a boat sinks or is significantly damaged by corrosion, or until fire, drowning, or electrocution results. Since galvanic isolators are installed in the AC grounding conductor and used in the boating industry to block DC galvanic current, the integrity of the boat's AC grounding conductor should never be compromised. Therefore, as was recognized by the invention disclosed in U.S. Pat. No. 5,746,008 of Landreth, which is hereby deemed incorporated herein by reference, there is a need in the boat industry for an apparatus that determines if a boat's galvanic isolator is operational, and generates a signal if it is not. The '008 patent disclosed an electrical integrity test system for boats that checks the integrity of galvanic isolators installed on boats connected to shore power. The present invention improves the electrical integrity test system of the '008 patent by recognizing that when a correctly wired boat is connected to the dock's electrical distribution system via the shore cord, occasional variations in the conduction level are encountered during testing of the boat's galvanic isolator. The variations in conduction of correctly wired boats vary from boat to boat, marina to marina, and boat to marina. The present invention further recognizes that the variations in conduction are caused by the entire grounding system to which the boat is connected. A boat's grounding system includes: (1) the boat's negative DC electrical system where the galvanic isolator is connected, which includes the boat's metallic components which have an electrical potential that is determined by the combined composition of the boats metals; and (2) the shore green grounding conductor which is referenced to earth ground at some point on shore, and is connected to the boat' galvanic isolator on the side opposite to which the boat's negative DC electrical system is connected.

Thus, the galvanic isolator in a boat essentially lies between a boat's DC negative electrical system and earth ground. Thus, for a correctly installed galvanic isolator the voltage potential of the earth ground will unlikely be the same as the boat's DC negative potential, due to the presence of galvanic isolator between the two reference points, which creates a slightly different electrical potential between the two. The earth ground and the boat's underwater metallic fittings are both in contact with the water, which serves as the common conductor or electrolyte of the electrical circuit containing the galvanic isolator. This circuit could be viewed and modeled as including two batteries having slightly different potentials connected to opposed sides of the galvanic isolator with the water being the common electrical path between the two batteries.

The differential voltage potential across the galvanic isolator under normal operating conditions is low enough to keep the silicon diodes from conducting. This differential voltage potential of the earth ground to the boat's negative DC ground system varies continuously as a result of (1) changes in the salinity of the water, (2) velocity of the water moving around the boat, (3) number of boats sharing the common earth ground and (4) the combined electrical potential of all the surrounding boat's underwater fittings within the marina connected to the common earth ground.

As explained in detail in the '008 patent and by way of background, to determine the status of the boat's galvanic isolator, the test system, under the control of the embedded micro-controller, conducts a series of test. First the test system applies a voltage across the galvanic isolator with respect to the boat's negative DC system biasing one pair of the silicon diodes into conduction while evaluating the voltage drop across the galvanic isolator. The test system then applies a negative voltage across the galvanic isolator, biasing the remaining pair of diodes into conduction.

It is recognized by the present invention that the varying differential voltage across the galvanic isolator may occasionally make it difficult to bias the pair of diodes to the same conduction level each time during testing. For example, for a galvanic isolator installed in a boat docked at one marina, the test voltage applied across one pair of the galvanic isolator's diodes may generate a voltage drop across the galvanic isolator of 1.50 volts. The same boat, when moved to another marina and connected to its electrical distribution service, under the same testing conditions of the galvanic isolator, the measured voltage drop across the galvanic isolator may be 1.30 volts. Additionally, different voltage drops across galvanic isolators may be seen in different boats next to one another in the same marina. In some cases, the measured voltage drop may be sufficiently lower.

As stated earlier, the biasing voltage characteristics range for a pair of series diodes is approximately 0.9–1.6 volts. If one of the diodes were shorted this voltage range would be approximately 0.45–0.85 volts. When the measured voltage across the galvanic isolator is in the lower voltage conduction level (0.9–1.20 volts), it is more difficult to determine if the measured voltage drop implies the diodes are in a low conduction state and the integrity of the galvanic isolator is intact or if one diode may be shorted. In other words, a single shorted diode is the hardest failed condition to detect when testing a galvanic isolator.

With the foregoing in mind, it becomes an object of the present invention to reliably and accurately determine the difference between a normal voltage drop and voltage drops across a galvanic isolator indicative of galvanic isolator fault.

Figure 1:
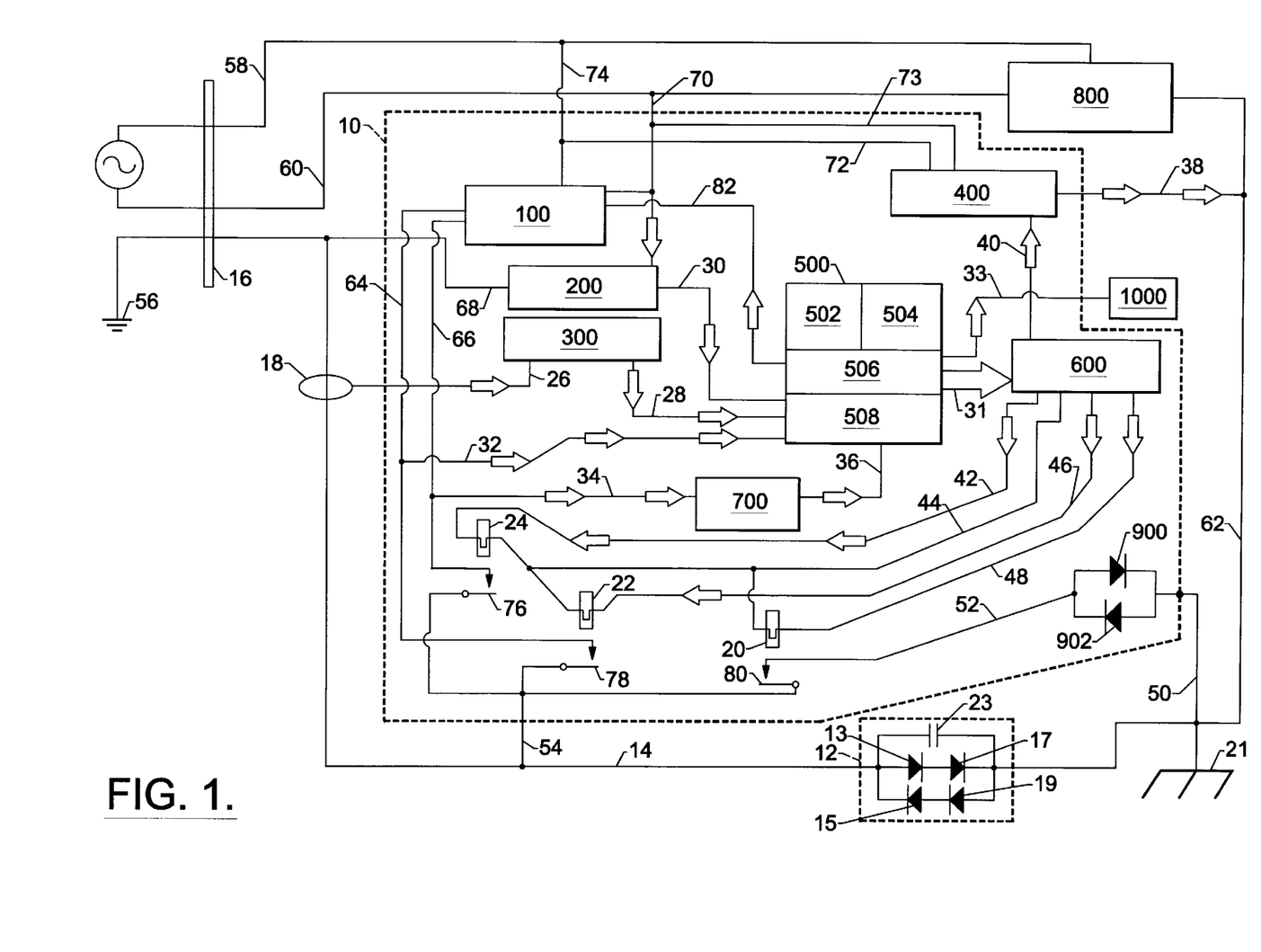
FIG. 1 is a block diagram representation of the components of the electrical integrity test system for boats employing the reference diodes of the present invention.
Figure 2:
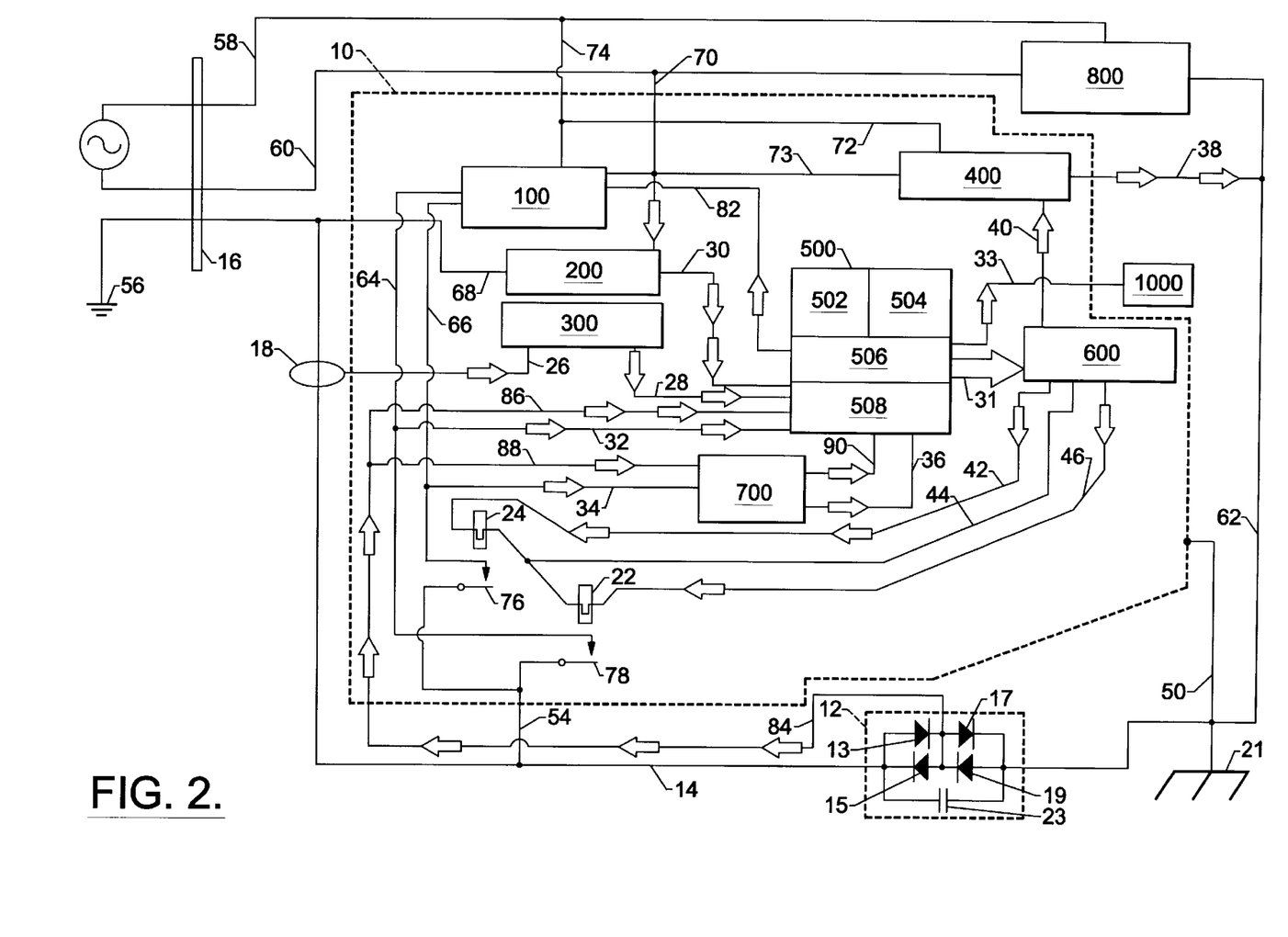
FIG. 2 is a block diagram representation of the electrical integrity test system for boats utilizing one individual diode of each set of diodes within the isolator as the reference diodes and additional analog inputs to the test system connected between each cathode-anode junction of each set of the galvanic isolator's series diodes.

It is another object of the invention to use two single silicon diodes as reference diodes and means to compare the measured voltage drop across the galvanic isolator's two series diodes and the measured voltage drop across a single reference diode. The single reference diodes may be part of the invention present circuitry as shown in FIG. 1, or two single diodes within the galvanic isolator under test could be utilized as the reference diodes as shown in FIG. 2 and further described herein.

SUMMARY OF THE INVENTION

The circuitry of the present invention evaluates, (1) the polarity of the dock's electrical distribution system, (2) the integrity of a boat's electrical distribution system, (3) the AC grounding system when the boat is connected to a dock's electrical distribution system, and (4) the integrity of the boat's galvanic isolator. The present invention includes a galvanic isolator integrity-detecting circuit, which includes reference diodes, a polarity detecting circuit, an AC ground detecting circuit, and a momentary AC inducing circuit. A system micro-controller controls the sequence of operation of the system as well as contains integral analog-to-digital converters, RAM memory registers for storing voltage measurements and memory for storing executable program code. The micro-controller used by the present invention can be a forty pin chip with eight analog A/Ds such as Microchip's micro-controller Model No. PIC16C74A or any other microcontroller having similar data storage and processing capabilities. The microcontroller utilizes a crystal or resonator (not shown) as its clock source. The reference diodes are opposing single silicon diodes placed in parallel with the boat's galvanic isolator. The use of reference diodes provides a known reference point for each test sequence independent of the different conduction levels of the galvanic isolator under test. Therefore, the present invention establishes acceptable test parameters for individual tests instead of a defined voltage range for all test conditions.

At some point during the test mode, the reference diodes are connected by means of the relay into the boat's circuit in parallel with the two series diodes within the galvanic isolator. The test voltage is applied across the galvanic isolator with the reference diode in parallel and the voltage drop across the reference diode is measured by means of the microcontroller's integral analog-to-digital converter (ADC). The measured voltage is stored in a RAM data register within the controller. The reference diode is then removed from the system under test and the test voltage is once again applied across the two diodes within the galvanic isolator and the voltage drop is measured by means of the microcontroller's ADC. The previous measured voltage across the reference diode is retrieved from the RAM data register and a software comparison is made between the measured voltage drop across the galvanic isolator's two series diodes and the measured voltage drop across the reference diode. Since both voltage measurements were made under identical and actual test conditions, there will be a distinct difference between the two measured voltage drops regardless of the level of conduction, since the differential potential between earth ground and the boat's negative DC ground is the same for both the reference diode and the diodes of the galvanic isolator. For an isolator in good operating condition, the reference diode voltage drop will be approximately ½ of the measured voltage drop across the galvanic isolator. Should the two measured voltage drops be very close to the same, the test device would use this as grounds for failing the galvanic isolator due to a shorted diode within the galvanic isolator. A measured voltage drop across a pair of the galvanic isolator's diodes of approximately 5 volts, in this case the circuit test voltage, would indicate an open-circuited diode within the galvanic isolator. A measured voltage of approximately 0 volts would indicate a completely shorted galvanic isolator.

The present invention will automatically conduct a test cycle when plugged into the marina shore power outlet. The executable program code allows for the system to execute a complete test sequence or partial sequence at various times as indicated in the program code. A test button (not shown) will allow the operator to initiate a test sequence at any time.

DETAILED DESCRIPTION OF PREFERRED EMBODIMENTS OF THE INVENTION

FIG. 1 is a block diagram representation of an illustrative embodiment of the electrical integrity test system 10 of the invention as applied to a boat. The boat's electrical system includes a galvanic isolator 12, with optional capacitor 23, connected in series with the boat's AC grounding conductor 14 between boat DC ground 21 and the earth ground 56 by means of the ground pin of the boat's electrically insulated shore power inlet 16. Shore power hot and neutral are supplied to the boat's electrical distribution panel 800 by means of conductors 58 and 60. AC electrical system distribution panel 800 safety ground conductor is connected to the boat's DC ground 21 by conductor 62.

The galvanic isolator as shown in FIGS. 1 and 2 consists of silicon diodes and may employ an optional capacitor. Therefore, to accurately model the electrical characteristics of the galvanic isolator, the "reference diodes", which may also be referred to herein as the "referenced model", are also comprised of silicon diodes. Silicon diodes, SCRs, Traics, etc. are semi-conductor type devices although SCRs and TRIAC's are typically referred to as thyristor devices. Likewise, the "reference model" could employ different types of semi-conductor or thyristic devices that accurately model the electrical characteristics of the galvanic isolator. The scope of this application is not to be restricted to only galvanic isolators consisting of silicon diodes but is to include any type of semi-conductor device. Therefore, from this point, "galvanic isolator" will imply a galvanic isolator employing any semi-conductor type device.

The electrical integrity test system 10, also referred to herein as "test system", is electrically referenced to the boat's DC ground 21 along line 50 and comprised of the following components and circuits. Test system DC power supply 100 is connected to the hot and neutral conductors 58,60 by conductors 74,70 and provides two independent DC outputs. One output (not shown) provides power to operate the system's electronic circuits. The second output is activated by micro-controller 500 along line 82 only during the testing cycle providing a positive 5VDC on conductor 64 and negative 5VDC on conductor 66. The positive and negative 5V DC are utilized to bias the galvanic isolator 12 into conduction during the test cycle through relays 24,22 and conductor 54 as discussed below in more detail. Micro-controller 500 includes executable program code 502, RAM Data Memory Registers 504 (RAM), digital output 506, and an integral A/D converter 508 (ADC).

Reverse Polarity Detection Circuit 200 is connected between the systems neutral conductor 60 by conductor 70 and the boat's AC grounding conductor 14 by conductor 68 and provides an analog output through conductor 30 to micro-controller 500 integral A/D converter 508 (ADC). The converted analog voltage is evaluated by the micro-controller 500 to determine when the shore power supply conductors are reversed. Micro-controller 500 provides digital output 506 through conductor 33 to LED Display 1000 to alert the operator of this condition.

Ground Current Sensing Circuit 300 connected to current transformer 18 by conductor 26 provides an analog output through conductor 28 to micro-controller 500 integral ADC 508 when AC ground currents are present.

Momentary AC Current Inducing Circuit 400 is connected to AC hot conductor by lines 72, 74 to AC neutral conductor by lines 73, 70 and controlled along line 40 through the Relay Control Interface Circuit 600 by the micro-controller 500. Depending on the polarity of the shore power as determined by the Reverse Polarity Detection Circuit 200, the microcontroller 500 provides a signal along line 31 to connect either the AC hot, line 72 or AC neutral, line 73 conductor to the Momentary AC Current Inducing Circuit. The Momentary AC Current Inducing Circuit places a small momentary AC signal into the boat's DC ground 21 on conductors 38 and 62. If an adequate AC ground exists the momentary AC signal is detected by the current transformer 18 and ground sensing circuit 300 and an analog voltage is provided to the ADC 508 input of the microcontroller 500 by line 28. If a momentary AC signal is not detected by the current transformer 18 thereby providing an analog signal from the Ground Current Sensing Circuit 300 on line 28 back to the micro-controller 500, the micro-controller provides a digital output 506 to LED Display 1000 along 33 to alert the operator of the condition.

U.S. Pat. No. 5,748,008 of Landreth discloses one example of the detailed circuitry of the Reverse Polarity Detection Circuit, Ground Current Sensing Circuit and the Momentary AC Current Inducing Circuit. Again, referring to FIG. 1, the isolator integrity-detecting circuitry of the present invention is comprised of the following components, power supply 100, relays 20, 22 and 24; Unity Gain Inverting Amplifier Circuit 700; Silicon Reference Diodes 900 and 902; Relay Control Interface Circuitry 600 and Microcontroller 500.

Micro-controller 500 initiates the testing and evaluation of all circuits including the boat's galvanic isolator 12, by first testing galvanic isolator 12 when it is in a static state. Micro-controller 500 first provides a digital output 506 through line 31 to the Relay Control Interface Circuit 600 which energizes relay 22 by lines 44 and 46 causing contact 78 to close. To determine if galvanic isolator 12 is in some level of conduction as a result of AC leakage current or a DC galvanic voltage while in the static state, the voltage drop across the galvanic isolator 12 series diodes 13, 17 is received at the integral ADC 508 by means of line 14, 54 and 32. Microcontroller 500 makes a software comparison between the measured static voltage drop across the galvanic isolator 12 series diodes 13, 17 to a predefined value of 1.1 V stored in a RAM data register. Internal software flags are set if the measured voltage drop exceeds the 1.1 V indicating galvanic isolator 12 is in a static state of conduction allowing the flow of galvanic currents.

Referring again to FIG. 1, the micro-controller 500 provides a digital signal on line 82 turning on power supply 100 which provides a positive 5 VDC, with respect to the boat's DC ground, across the galvanic isolator 12 by means of line 64, through closed contact 78 and conductors 54 and 14 thereby forcing the galvanic isolator's series diodes 13, 17 into some conduction level. The voltage drop across galvanic isolator 12 series diodes 13, 17 is measured at the integral ADC 508 by means of line 32. Micro-controller 500 stores this measured voltage in one of its RAM Data Memory Registers 504 (RAM). Once this value is stored in RAM 504, micro-controller 500 removes the digital output 506 along line 82, turning off power supply 100 removing the 5 VDC from across galvanic isolator 12.

Micro-controller 500 provides along line 31 digital output 506 to Relay Control Interface Circuit 600 which energizes relay 20 by lines 44 and 48 thereby closing contact 80 connecting the reference diodes 900 and 902 in parallel with the boat's galvanic isolator 12 by means of lines 50, 52, and conductors 54 and 14. With contacts 80 and 78 closed, micro-controller 500 provides a digital output 506 along line 82 to power supply 100. Power Supply 100 provides a positive 5 VDC along line 64, with respect to the boat's DC ground, across the galvanic isolator 12 and parallel reference diodes 900 and 902 by means of line 64, through closed contact 78 and conductors 54 and 14 thereby forcing the single reference diode 900 into some conduction level.

The voltage drop across single reference diode 900 is measured by integral ADC 508 by means of line 14, 54 and 32. Micro-controller 500 stores this measured voltage in RAM 504. Micro-controller 500 removes all digital output 506 to Relay Control Interface Circuit 600 along line 31 and Power Supply 100 along line 82 therefore de-energizing relays 20 and 22 opening contacts 78, 80, and turning off the 5 VDC along line 64.

Micro-controller 500 recalls the stored values for voltage drops across the galvanic isolator 12 series diodes 13, 17 and the single reference diode 900 and uses these values to determine the status of the galvanic isolator 12 set of series diodes 13, 17. Software of micro-controller 500 evaluates the measured voltage drops are made as follows:

Condition 1; An initial voltage drop across galvanic isolator 12 series diodes 13, 17 of approximately 5VDC indicates at least one of the isolator 12 series diodes 13, 17 is open-circuit.

Condition 2; An initial voltage drop across galvanic isolator 12 series diodes 13, 17 of approximately 0VDC indicates both of the isolator 12 series diodes 13, 17 are shorted.

Condition 3; An initial voltage drop across galvanic isolator 12 series diodes 13, 17 approximately the same as the recorded voltage drop across the single reference diode 900, when placed in parallel with the galvanic isolator 12, indicates one of isolator 12 series diodes 13, 17 is shorted.

Condition 4; An initial voltage drop across galvanic isolator 12 series diodes 13, 17 approximately two times the recorded voltage drop across single reference diode 900, when placed in parallel with the galvanic isolator 12, indicates isolator 12 series diodes 13, 17 are operational and intact.

Software flags would be set by the micro-controller for failure conditions 1–3 for later use.

In order to evaluate the integrity of galvanic isolator 12 remaining pair of series diodes 15, 19 the micro-controller initiates another test cycle as described as follows. Referring again to FIG. 1, the micro-controller provides digital output 506 along line 31 to Relay Control Interface Circuit 600 energizing relay 24 by lines 42 and 44 thereby closing contact 76. To determine if galvanic isolator 12 pair of series diodes 15, 19 are in some level of conduction as a result of AC leakage current or a DC galvanic voltage while in the static state, the voltage drop across the galvanic isolator 12 series diodes 15, 19 is received at the Unity Gain Inverting Amplifier 700 along lines 14, 54 and 34. Unity Gain Inverting Amplifier 700 provides a positive output voltage, having a magnitude equal to the negative voltage drop across isolator 12 series diodes 15, 19 and transmits the positive voltage to the integral ADC 508 via line 36. Micro-controller 500 compares the measured static voltage drop across galvanic isolator 12 series diodes 15, 19 to a predefined value of 1.1 V stored in RAM 504. Internal software flags are set if the measured voltage drop exceeds the 1.1 V indicating the galvanic isolator 12 is in a static state of conduction allowing the flow of galvanic currents.

Micro-controller 500 provides a digital signal on line 82 turning on Power Supply 100. Power Supply 100 provides a negative 5 VDC, with respect to the boat's DC ground, across the galvanic isolator 12 by means of line 66, through closed contact 76 and conductors 54 and 14 thereby forcing galvanic isolator 12 series diodes 15, 19 into some conduction level.

The negative voltage drop across the galvanic isolator 12 series diodes 15, 19 is received at Unity Gain Inverting Amplifier 700 by means of lines 14, 54 and 34. Unity Gain Inverting Amplifier 700 provides a positive output voltage, having a magnitude equal to the negative voltage drop across isolator 12 series diodes 15, 19 and transmits the positive voltage to integral ADC 508 via line 36. Micro-controller 500 stores this measured voltage in RAM 504. Once this value is stored in RAM 504, the micro-controller 500 removes the digital output 506 along line 83 turning off the negative 5 VDC from across galvanic isolator 12.

Micro-controller 500 provides digital output 506 to Relay Control Interface Circuit 600 which energizes relay 20 by lines 44 and 48 thereby closing contact 80 connecting the reference diodes 900 and 902 in parallel with the boat's galvanic isolator 12 by means of lines 50, 52, closed contact 80, and conductors 54 and 14. With contacts 80 and 76 closed, micro-controller 500 provides digital output 506 along line 82 turning on Power Supply 100. Power Supply 100 provides negative 5 VDC, with respect to the boat's DC ground, across galvanic isolator 12 and parallel reference diodes 900 and 902 via line 64, thereby forcing single reference diode 902 into some conduction level.

The negative voltage drop across single reference diode 902 in parallel with the galvanic isolator 12 series diodes 15, 19 is received at Unity Gain Inverting Amplifier 700 by means of lines 14, 54 and 34. Unity Gain Inverting Amplifier 700 provides a positive output voltage, having a magnitude equal to the negative voltage drop across galvanic isolator 12 series diodes 15, 19 and transmits the positive voltage to the integral ADC 508 via line 36. Micro-controller 500 stores this measured voltage in RAM 504.

Micro-controller 500 removes all digital output 506 to Relay Control Interface Circuit 600 along line 31 and Power Supply 100 along line 82, therefore de-energizing relays 20 and 24 and opening contacts 76 and 80. Micro-controller 500 then recalls the stored values and uses them to determine the status of the galvanic isolator 12 series diodes 15, 19. The software of micro-controller 500 evaluates the measured voltage drops are made as follows:

Condition 1; An initial voltage drop across galvanic isolator 12 series diodes 15, 19 of approximately 5VDC indicates at least one of isolator 12 series diodes 15, 19 is an open-circuit.

Condition 2; An initial voltage drop across galvanic isolator 12 series diodes 15, 19 of approximately 0VDC indicates both of isolator 12 series diodes 15, 19 are shorted.

Condition 3; An initial voltage drop across galvanic isolator 12 series diodes 15, 19 approximately the same as the recorded voltage drop across single reference diode 902, when placed in parallel with galvanic isolator 12, indicates one of isolator 12 series diodes 15 is shorted.

Condition 4; An initial voltage drop across galvanic isolator 12 series diodes 15, 19 approximately two times the recorded voltage drop across the single reference diode 902, when placed in parallel with galvanic isolator 12, indicates isolator 12 series diodes 15, 19 are operational and intact.

Upon completion of evaluating galvanic isolator 12, micro-controller 500 checks all software flags then provides a digital output 506 along line 33 to LED Display 1000 to notify the operator if any single or combination of the unacceptable conditions noted above are detected.

FIG. 2 illustrates a second embodiment of the present invention. FIG. 2 is identical to FIG. 1 except for adding line 84, which provides two more analog channels 86, 88 and removal of reference diodes 900 and 902. For simplicity, components common to both FIGS. 1 and 2 are numbered identically.

The additional conductor 84 provides a means to evaluate the voltage drop across individual diodes 17, 19 while still being able to evaluate the voltage drop across each series pair of diodes, therefore; providing another means of determining the status of the galvanic isolator.

The second embodiment of the present invention does not rely on reference diodes 900 and 902 shown in FIG. 1. However, the second embodiment utilizes the galvanic isolators single diodes 17, 19 along line 84 as a known reference source as previously described.

Referring to FIG. 2, during testing of galvanic isolator 12, micro-controller 500 provides digital signals to close relay 22, closing contact 78 and turning on Power Supply 100 via line 82. Power Supply 100 provides a positive 5 VDC by lines 64, 54, and 14, with respect to the boat's DC ground 21, across galvanic isolator 12, biasing series diodes 13, 17 into conduction.

The voltage drop across galvanic isolator's 12 series diode 13,17 is measured by integral ADC 508 by means of lines 14, 54 and 32. Micro-controller 500 stores this measured voltage in RAM 504. The voltage drop across galvanic isolator's 12 single diode 17 is measured by integral ADC 508 by means of lines 84,86. Micro-controller 500 stores this measured voltage in RAM 504. Micro-controller 500 removes digital output 506 to Relay Control Interface Circuit 600 and Power Supply 100 on line 82, thereby de-energizing relays 22 opening contact 78 and shutting down the 5 VDC test voltage.

Micro-controller 500 recalls the stored values and uses these to determine the status of the galvanic isolator 12 series diodes 13,17. The software of the micro-controller evaluate the voltage drops as follows:

Condition 1; An initial voltage drop across galvanic isolator 12 series diodes 13,17 of approximately 5VDC indicates at least one of isolator 12 series diodes 13,17 is open-circuit.

Condition 2; An initial voltage drop across galvanic isolator 12 series diodes 13,17 of approximately 0VDC indicates both of isolator 12 series diodes 13,17 are shorted.

Condition 3; An initial voltage drop across galvanic isolator 12 series diodes 13,17 approximately the same as the recorded voltage drop across galvanic isolator 12 diode 17 indicates diode 13 of galvanic isolator 12 is shorted.

Condition 4; An initial voltage drop of approximately 0 VDC across the single galvanic isolator 12 diode 17 indicates the galvanic isolator 12 single diode 17 is shorted.

Condition 5; An initial voltage drop across galvanic isolator 12 series diodes 13,17 approximately two times the recorded voltage drop across the single galvanic isolator 12 diode 17 indicates galvanic isolator series diodes 13,17 are operational and intact.

Software flags are set accordingly.

To complete the testing of the galvanic isolator, micro-controller 500 provides digital signals to close relay 24, close contact 76 and turn on Power Supply 100 by line 82 thereby providing a negative 5 VDC, by lines 66, 54, and 14, with respect to the boat's DC ground 21 across galvanic isolator 12 biasing series diodes 15,19 into conduction.

The negative voltage drop across galvanic isolator 12 single diode 19 is received at the Unity Gain Inverting Amplifier 700 by means of lines 84,88. The negative voltage drop across galvanic isolator 12 series diodes 15, 19 is received at Unity Gain Inverting Amplifier 700 by means of lines 14, 54 and 34. The Unity Gain Inverting Amplifier 700 provides a positive output voltage, having a magnitude equal to the negative voltage drop across the galvanic isolator series diodes 15,19 by means of lines 36 and a positive voltage equal to the negative voltage drop across the single diode 19 by means of line 90. Micro-controller 500 stores these measured voltages in RAM 504. Micro-controller 500 then removes digital output 506 to Relay Control Interface Circuit 600 and Power Supply 100 on line 82 thereby de-energizing relays 24 opening contact 76 and shutting down the negative 5 VDC test voltage.

Micro-controller 500 recalls the stored values and uses these to determine the status of galvanic isolator 12 series diodes 15,19. Software of the micro-controller evaluates measured voltage drops as follows:

Condition 1; An initial voltage drop across galvanic isolator 12 series diodes 15,19 of approximately 5VDC indicates at least one of galvanic isolator 12 series diodes 15,19 is open-circuit.

Condition 2; An initial voltage drop across galvanic isolator 12 series diodes 15,19 of approximately 0VDC indicates both of galvanic isolator 12 series diodes 15,19 are shorted.

Condition 3; An initial voltage drop across galvanic isolator 12 series diodes 15,19 approximately the same as the recorded voltage drop across single galvanic isolator 12 diode 19 indicates diode 15 of isolator 12 series diodes 15, 19 is shorted.

Condition 4; An initial voltage drop of approximately 0 VDC across one single galvanic isolator 12 diode 19 indicates isolator 12 diode 19 is shorted.

Condition 5; An initial voltage drop across galvanic isolator 12 series diodes 15,19 approximately two times the recorded voltage drop across single galvanic isolator 12 diode 19 indicates galvanic isolator 12 series diodes 15,19 are operational and intact.

The micro-controller checks the software flags and provides an appropriate digital output 506 to the LED Display 1000.

While the invention has been described with reference to specific embodiments thereof, it will be appreciated that numerous variations, modifications, and embodiments are possible, and accordingly, all such variations, modifications, and embodiments are to be regarded within the spirit and scope of the invention.

What is claimed is:

1. An apparatus for applying a series of interrelated electrical tests to AC circuitry and an associated galvanic isolator having series semi-conductors, normally operative and arranged to block passage of DC currents in both directions and to permit passage of AC currents in both directions and to permit passage of AC currents through the galvanic isolator to earth ground, said apparatus comprising:
  a) means for applying a DC voltage of selected first polarity across a first silicon diode reference semi-conductor and of sufficient magnitude to establish what would be expected to be a normal voltage drop corresponding thereto;
  b) means for applying a DC voltage of said first polarity across said galvanic isolator and of sufficient magnitude to establish what would be expected to be a normal voltage drop corresponding thereto;
  c) means for comparing the voltage drop across said galvanic isolator with said voltage drop across said first silicon diode reference semi-conductor;
  d) means for applying a DC voltage of selected second polarity opposite said first polarity across a second silicon diode reference semi-conductor and of sufficient magnitude to establish what would be expected to be a normal voltage drop corresponding thereto;
  e) means for applying a DC voltage of said second polarity across said galvanic isolator and of sufficient magnitude to establish what would be expected to be a normal voltage drop corresponding thereto;
  f) means for comparing the voltage drop across said second silicon diode reference semi-conductor with said voltage drop across said galvanic isolator; and
  g) means for indicating whether the voltage drops corresponding to application of said DC voltages of said first and second polarities across said galvanic isolator and across said first and second silicon diode reference semi-conductors correspond to what would be normally expected.

2. An apparatus for testing AC circuitry and an associated galvanic isolator as claimed in claim 1, further comprising means for evaluating the voltage drop across said galvanic isolator while in a static state and comparing the result of evaluating said voltage drop to a pre-defined maximum limit.

3. An apparatus for testing AC circuitry and an associated galvanic isolator as claimed in claim 1, further comprising an AC shore power distribution system and means for determining whether the on-shore neutral and hot AC supply conductors of said AC shore power distribution system are reversed.

4. An apparatus for testing AC circuitry and an associated galvanic isolator as claimed in claim 1, further comprising means for detecting both the magnitude and length of time AC current flows in the grounding conductor connecting said galvanic isolator and said earth ground and when said magnitude of time exceeds some predetermined level thereby detecting such excess magnitude or time and responsive thereto by energizing a signaling means.

5. an apparatus for testing AC circuitry and an associated galvanic isolator as claimed in claim 1, further comprising means for inducing a momentary AC current into the grounding conductor connecting said galvanic isolator and said earth ground, detecting whether such induced AC current flows to said earth ground and creating a signal responsive to the absence of such flow.

6. An apparatus for testing AC circuitry and an associated galvanic isolator as claimed in claim 1, wherein said first silicon diode reference semi-conductor is one of a first set of said series semi-conductors.

7. An apparatus for testing AC circuitry and an associated galvanic isolator as claimed in claim 1, wherein said second silicon diode reference semi-conductor is one of a second set of said series semi-conductors.

8. An apparatus for testing AC circuitry and an associated galvanic isolator as claimed in claim 1, wherein said first and second silicon diode reference semi-conductors are placed in parallel with said galvanic isolator.

9. An apparatus for testing AC circuitry and an associated galvanic isolator as claimed in claim 1 including control means for controlling the sequence of operation of each of said other means.

10. An apparatus for testing AC circuitry and an associated galvanic isolator as claimed in claim 1 including means for storing said voltage drops thereby enabling said means for comparing and indicating to be operative with respect to said stored voltage drops.

11. A method for applying a series of interrelated electrical tests to AC circuitry and an associated galvanic isolator having series semi-conductors comprising:
  a) applying a DC voltage of selected first polarity across a first silicon diode reference semi-conductor and of sufficient magnitude to establish what would be expected to be a normal voltage drop corresponding thereto;
  b) applying a DC voltage of said first polarity across said galvanic isolator and of sufficient magnitude to establish what would be expected to be a normal voltage drop corresponding thereto;
  c) comparing the voltage drop across said galvanic isolator with said voltage drop across said first silicon diode reference semi-conductor;
  d) applying a DC voltage of selected second polarity opposite said first polarity across a second silicon diode reference semi-conductor and of sufficient magnitude to establish what would be expected to be a normal voltage drop corresponding thereto;
  e) applying a DC voltage of said second polarity across said galvanic isolator and of sufficient magnitude to establish what would be expected to be a normal voltage drop corresponding thereto;
  f) comparing the voltage drop across said second silicon diode reference semi-conductor with said voltage drop across said galvanic isolator;
  g) determining whether the voltage drops across said galvanic isolator and said first silicon diode reference semi-conductor when said DC voltage of said first polarity is applied thereto are each within a predetermined range selected to indicate whether one of the galvanic isolator's series semi-conductors is shorted; and
  h) determining whether the voltage drops across said galvanic isolator and said second silicon diode reference semi-conductor when said DC voltage of said second polarity is applied thereto are each within a predetermined range selected to indicate whether one of the galvanic isolator's series semi-conductors is shorted.

12. A method for testing a galvanic isolator as claimed in claim 11, further comprising determining whether the voltage drop across said galvanic isolator is sufficiently higher than the voltage drop across said first silicon diode reference semiconductor, to indicate whether or not a first set of galvanic isolator series semi-conductors is operational.

13. A method for testing a galvanic isolator as claimed in claim 11, further comprising determining whether the voltage drop across said galvanic isolator is sufficiently higher than the voltage drop across said second silicon diode reference semi-conductor, to indicate whether a second set of galvanic isolator series semi-conductors is operational.

14. A method for applying a series of interrelated electrical tests to AC circuitry and an associated galvanic isolator as claimed in claim 11 including the step of storing said voltage drops so as to enable said comparing and determining to be made with respect to said stored voltage drops.

15. A method for applying a series of interrelated electrical tests to AC circuitry and an associated galvanic isolator having series semi-conductors comprising:
   a) applying a DC voltage of selected first polarity across said galvanic isolator and of sufficient magnitude to establish what would be expected to be a normal voltage drop corresponding thereto;
   b) if said galvanic isolator is determined by said first step to be neither open circuited or short-circuited, applying a DC voltage of said first polarity across a first silicon diode reference semi-conductor and of sufficient magnitude to establish what would be expected to be a normal voltage drop corresponding thereto;
   c) comparing the voltage drop across said galvanic isolator with the voltage drop across said first silicon diode reference semi-conductor;
   d) applying a DC voltage of selected second polarity opposite said first polarity across said galvanic isolator and of sufficient magnitude to establish what would be expected to be a normal voltage drop corresponding thereto;
   e) if said galvanic isolator is determined by said step d) to be neither open circuited or short-circuited, applying a DC voltage of said second polarity opposite said first polarity across a second silicon diode reference semi-conductor and of sufficient magnitude to establish what would be expected to be a normal voltage drop corresponding thereto;
   f) comparing the voltage drop across said galvanic isolator with the voltage drop across said first silicon diode reference semi-conductor;
   g) determining whether the voltage drops across said galvanic isolator and said first silicon diode reference semi-conductor when said DC voltage of said first polarity is applied thereto are each within a predetermined range selected to indicate whether one of the galvanic isolator's series semi-conductors is shorted; and
   h) determining whether the voltage drops across said galvanic isolator and said second silicon diode reference semi-conductor when said DC voltage of said second polarity is applied thereto are each within a predetermined range selected to indicate that one of the galvanic isolator's series semi-conductors is shorted.

16. A method for applying a series of interrelated electrical tests to AC circuitry and an associated galvanic isolator as claimed in claim 15 including the step of storing said voltage drops so as to enable said comparing and determining to be made with respect to said stored voltage drops.

17. An apparatus for applying a series of interrelated electrical tests to AC circuitry associated with a galvanic isolator connected on one side through a grounding conductor to earth ground and having series semi-conductors and being normally operative and arranged to block passage of DC currents in both directions, to permit passage of AC currents in both directions and to permit passage of AC currents through the galvanic isolator to earth ground and which tests include a test for operability of said isolator, said apparatus comprising:
   a) silicon diode reference semi-conductor means electrically accessible for said tests;
   b) means for selectively applying to either or both said isolator and silicon diode reference means a DC voltage of either first or second polarity;
   c) means for comparing the voltage drops produced by application of said DC voltage to said isolator and silicon diode reference means; and
   d) means for determining from such comparison the operability of either or both said AC circuitry and isolator.

18. An apparatus for applying a series of interrelated electrical tests to AC circuitry associated with a galvanic isolator as claimed in claim 1 including means for storing said voltage drops thereby enabling said means for comparing and determining to be operative with respect to said stored voltage drops.

19. An apparatus for testing AC circuitry and an associated galvanic isolator as claimed in claim 1 wherein said AC circuitry comprises a boat's on-board electrical system and including:
   a) means for determining whether an associated on-shore neutral conductor and hot AC supply conductors are reversed by establishing a connection between said neutral conductor and grounding conductor; and
   b) means operative in the event said neutral and hot conductors are reversed for detecting current flowing therebetween and directing said flow of current to a signaling means responsive thereto and operatively associated therewith.

20. An apparatus for testing AC circuitry and an associated galvanic isolator as claimed in claim 18 including:
   a) means for inducing a momentary AC current into said grounding conductor at a first location on said grounding conductor;
   b) circuit means at a second location on said grounding conductor closer to said earth ground than said first location for detecting whether such induced AC current flows to said earth ground; and
   c) means for creating a signal responsive to the absence of such flow.

21. An apparatus for testing AC circuitry and an associated galvanic isolator as claimed in claim 18 including:
   a) means for inducing an AC current at a location connected to both said galvanic isolator and said earth ground;
   b) means for detecting both the magnitude of said induced AC current and length of time said induced AC current flows to said earth ground; and
   c) means operative when said magnitude or time exceed some predetermined level for detecting such excess magnitude or time and responsive thereto energizing a signaling means operatively associated therewith.

22. A method for utilizing a selected number of silicon diode reference semi-conductors for testing selected components of a boat's on-board electrical system having an on-board galvanic isolator connected on one side through a grounding conductor to an on-shore earth ground and on an opposite side to a DC ground forming part of a boat's on-board electrical system, said galvanic isolator comprising solid state elements normally operative to block passage of DC currents in both directions and to permit passage of AC currents through said galvanic isolator to said earth ground, comprising:

a) applying a DC voltage of selected polarity across a silicon diode reference semi-conductor and of sufficient magnitude to establish what would be expected to be a normal voltage drop corresponding thereto;

b) applying a DC voltage of selected first polarity across said galvanic isolator and of sufficient magnitude to establish what would be expected to be a normal voltage drop corresponding thereto;

c) comparing the voltage drop across said galvanic isolator when said DC voltage of selected first polarity was applied with the voltage drop across said silicon diode reference semi-conductor;

d) applying a DC voltage of selected second polarity opposite said first polarity across said galvanic isolator and of sufficient magnitude to establish what would be expected to be a normal voltage drop corresponding thereto;

e) comparing the voltage drop across said galvanic isolator when said DC voltage of selected second polarity was applied with said voltage drop across said silicon diode reference semi-conductor; and f) utilizing indicating means for indicating whether the voltage drops corresponding to application of said DC voltage of first and second polarities across said galvanic isolator and voltage drop corresponding to application of said DC voltage of selected polarity across said silicon diode reference semi-conductor correspond to what would be normally expected.

23. A method as claimed in claim 22 including the step of storing said voltage drops thereby enabling said comparing and indicating to be made with respect to said stored voltage drops.

24. A method as claimed in claim 22 including the steps of:

a) determining whether an associated on-shore neutral conductor and hot AC supply conductors are reversed by establishing a connection between said neutral conductor and grounding conductor; and b) in the event said neutral and hot conductors are reversed detecting current flowing therebetween and directing said flow of current to a signaling means responsive thereto and operatively associated therewith.

25. A method as claimed in claim 22 including the steps of:

a) inducing a momentary AC current into said grounding conductor at a first location on said grounding conductor;

b) utilizing circuit means at a second location on said grounding conductor closer to said earth ground than said first location for detecting whether such induced AC current flows to said earth ground; and c) creating a signal responsive to the absence of such flow.

26. A method as claimed in claim 22 including the steps of:

a) detecting both the magnitude and length of time said AC currents flow to said earth ground; and b) when said magnitude or time exceed some predetermined level detecting such excess magnitude or time and responsive thereto energizing a signaling means operatively associated therewith.

* * * * *

UNITED STATES PATENT AND TRADEMARK OFFICE
CERTIFICATE OF CORRECTION

PATENT NO.   : 6,265,879 B1
DATED        : July 24, 2001
INVENTOR(S)  : Keith W. Landreth It is certified that error appears in the above-identified patent and that said Letters Patent is hereby corrected as shown below:

Column 5,
Line 38, "Traics" should read -- TRIACS --.
Line 54, "74, 70'" should read -- 74, 70 --.

Column 14,
Line 19, "claim 1" should read -- claim 17 --.
Line 24, "claim 1" should read -- claim 17 --.
Line 37, "claim 18" should read -- claim 17 --.
Line 49, "claim 18" should read -- claim 17 --.

Signed and Sealed this

Fifth Day of March, 2002

Attest:

Attesting Officer

JAMES E. ROGAN
Director of the United States Patent and Trademark Office